United States Patent [19]

Yamaguchi et al.

[11] 4,443,360

[45] Apr. 17, 1984

[54] OIL-SOLUBLE ZINC CYCLIC HYDROCARBYL DITHIOPHOSPHATE-SUCCINIMIDE COMPLEX AND LUBRICATING OIL COMPOSITIONS CONTAINING SAME

[75] Inventors: Elaine S. Yamaguchi, El Cerrito; Thomas V. Liston, San Rafael, both of Calif.

[73] Assignee: Chevron Research Company, San Francisco, Calif.

[21] Appl. No.: 369,706

[22] Filed: Apr. 19, 1982

[51] Int. Cl.$^3$ ............................................... C10M 1/48
[52] U.S. Cl. ............................... 252/46.7; 252/32.7 E; 252/389 A; 252/400 A; 260/429.9
[58] Field of Search ............. 252/32.7 E, 46.7, 389 A, 252/400 A; 260/429.9

[56] References Cited

U.S. PATENT DOCUMENTS

| | | | |
|---|---|---|---|
| 3,089,850 | 5/1963 | McConnell et al. | 252/32.7 E |
| 3,135,694 | 6/1964 | Loughran et al. | 252/32.7 E X |
| 3,284,354 | 11/1966 | Tunkel et al. | 252/32.7 E |
| 3,502,677 | 3/1970 | LeSuer | 252/32.7 E X |
| 3,652,616 | 3/1972 | Watson et al. | 252/46.7 X |
| 3,844,960 | 10/1974 | Breitigam et al. | 252/32.7 E |
| 3,846,317 | 11/1974 | Lintzenich | 252/46.7 |
| 4,306,984 | 12/1981 | Yamaguchi | 252/46.7 |

FOREIGN PATENT DOCUMENTS 1237581  6/1971  United Kingdom ........... 252/32.7 E

*Primary Examiner*—Andrew Metz
*Attorney, Agent, or Firm*—S. R. LaPaglia; J. M. Whitney; V. J. Cavalieri

[57] ABSTRACT

Oil-insoluble zinc salts of cyclic dithiophosphates are rendered oil soluble when combined to form a complex with alkenyl or alkyl mono- or bis-succinimides. Oil compositions containing this combination are useful as crankcase lubricants.

12 Claims, No Drawings

OIL-SOLUBLE ZINC CYCLIC HYDROCARBYL DITHIOPHOSPHATE-SUCCINIMIDE COMPLEX AND LUBRICATING OIL COMPOSITIONS CONTAINING SAME

BACKGROUND OF THE INVENTION

1. Field of the Invention

This invention relates to a combination of an oil-soluble zinc cyclic hydrocarbyl dithiophosphate and an alkenyl or alkyl succinimide and the use of said combination in lubricating oils employed for crankcase lubrication of internal combustion engines.

2. Description of the Prior Art

Metal dihydrocarbyl dithiophosphates are useful for a variety of purposes known in the art. The zinc hydrocarbyl dithiophosphates in particular are employed as oxidation and corrosion inhibitors in lubricating oil compositions. U.S. Pat. No. 3,089,850 teaches the preparation of metal cyclic hydrocarbyl dithiophosphates prepared by reacting a glycol with phosphorus pentasulfide followed by reaction with a basic metal compound.

There is a problem, however, with certain of the metal cyclic hydrocarbyl dithiophosphates of this reference in that they are essentially insoluble in lubricating oil formulations.

Thus, the insolubility and resulting essential nonuse of certain metal cyclic hydrocarbyl dithiophosphates is a severe drawback in the utility of these compounds in crankcase lubricants.

SUMMARY OF THE INVENTION

It has now been found that an oil-insoluble zinc cyclic hydrocarbyl dithiophosphate may be made oil soluble by forming a complex between the dithiophosphate and an alkenyl or alkyl mono- or bis-succinimide.

Thus, this invention relates to a lubricating oil composition comprising a major amount of an oil of lubricating viscosity and a minor proportion sufficient to inhibit oxidation and corrosion of a complex prepared by reacting:

(a) a zinc salt of a hydrocarbyl dithiophosphoric acid of the formula:

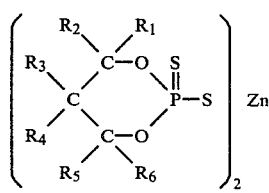

wherein $R_1$, $R_2$, $R_3$, $R_4$, $R_5$ and $R_6$ are the same or different and each is hydrogen or alkyl of 1 to 3 carbon atoms with the proviso that each of $R_1$ through $R_6$ cannot all be hydrogen at the same time; with (b) an oil-soluble alkenyl or alkyl mono- or bis-succinimide of the formula:

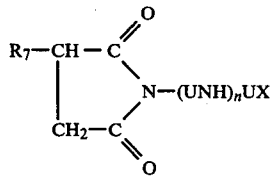

wherein X is amino or a group of the formula:

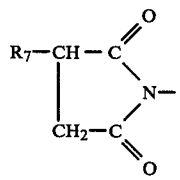

$R_7$ is an alkenyl or alkyl group containing from about 20 to 300 carbon atoms; U is alkylene containing 2 to 6 carbon atoms; and n is an integer of from 0 to 6;

wherein the weight ratio of (b) to (a) is in the range of 3:1 to 25:1, preferably 3:1 to 10:1.

DETAILED DESCRIPTION

The cyclic hydrocarbyl zinc dithiophosphates useful in the present invention are zinc salts of cyclic hydrocarbyl dithiophosphoric acids represented generally by the formula:

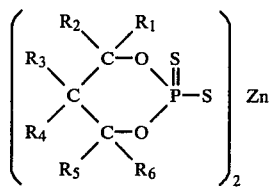

wherein $R_1$ through $R_6$ are defined above.

These compounds can be prepared by the reaction of a suitable glycol or mixture of glycols with phosphorus pentasulfide followed by reaction with a basic zinc compound. Methods to prepare these compounds are described in U.S. Pat. No. 3,089,850, and the disclosures thereof are incorporated herein by reference. Generally, according to this reference, cyclic hydrocarbyl dithiophosphoric acids are first prepared by reacting a glycol of the Formula II:

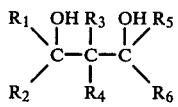

wherein $R_1$, $R_2$, $R_3$, $R_4$, $R_5$ and $R_6$ are as defined above, with phosphorus pentasulfide followed by reaction with a basic zinc compound. The reaction for preparation of the dithiophosphoric acid is carried out at a temperature in the range of 25° C. to 100° C., optionally in the presence of a solvent and at a mole ratio of glycol to phosphorus pentasulfide of 2:1.

For example, the cyclic hydrocarbyl dithiophosphoric acid may be prepared at a mole ratio of glycol to phosphorus pentasulfide of 2:1 by slowly and steadily adding the glycol (2 moles) to a toluene solution (about 600 ml) of the phosphorus pentasulfide (1 mole) at a temperature of from 40° C. to 113° C.

Representative of the glycols used to prepare the cyclic hydrocarbyl dithiophosphoric acid include 2,2-dimethyl-1,3-propanediol; 2-ethyl-2-methyl-1,3-propanediol; 2,2-diethyl-1,3-propanediol; 2-butyl-2-ethyl-1,3-propanediol; 2-ethyl-1,3-hexanediol; 2,4-pentanediol; 2,2,4-trimethyl-1,3-pentanediol; 5-methyl-2,4-hexanediol; and the like. Because of the proviso in the definition of $R_1$ through $R_6$, the 1,3-propanediol is specifically excluded.

The basic zinc compounds which are useful in this invention include those zinc salts which are capable of reacting with the dithiophosphoric acids such as zinc oxide, zinc hydroxide, zinc carbonate, zinc propylate, and the like.

The oil-soluble alkenyl or alkyl mono- or bis-succinimides which are employed in the additive combination of this invention are generally known as lubricating oil detergents and are described in U.S. Pat. Nos. 2,992,708; 3,018,291; 3,024,237; 3,100,673; 3,219,666; 3,172,892; and 3,272,746, the disclosures of which are incorporated by reference. These materials are prepared by reacting an alkenyl or alkyl-substituted succinic anhydride of the formula:

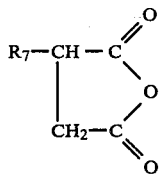

wherein $R_7$ is defined above, with a polyalkylene polyamine of the formula:

wherein U and n are defined above.

The alkylene group designated by U, which contains from 2 to 6 carbon atoms, may be straight chained or branched, but will usually be straight chained. Illustrative alkylene groups are ethylene, propylene, 1,2-propylene, tetramethylene, hexamethylene, etc. The preferred alkylene groups are from two to three carbon atoms, there being two carbon atoms between the nitrogen atoms.

Non-limiting examples of suitable amino compounds include: 1,2-diaminoethane; 1,3-diaminopropane; 1,4-diaminobutane; 1,6-diaminohexane; diethylene triamine; triethylene tetramine; tetraethylene pentamine; 1,2-propylene diamine; and the like.

A product comprising predominantly mono- or bis-succinimide can be prepared by controlling the molar ratios of the reactants. Thus, for example, if 1 mole of amine is reacted with 1 mole of the alkenyl or alkyl substituted succinic anhydride, a predominantly mono-succinimide product will be prepared. If 2 moles of the succinic anhydride are reacted per mole of polyamine, a bis-succinimide will be prepared.

The preparation of the alkenyl substituted succinic anhydride by reaction with a polyolefin and maleic anhydride has been described, e.g., U.S. Pat. Nos. 3,018,250 and 3,024,195. Reduction of the alkenyl substituted succinic anhydride yields the corresponding alkyl derivative. Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of two or more such olefins such as copolymers of: ethylene and propylene; butylene and isobutylene; etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, propylene and 1,4-hexadiene; etc.

The olefin polymers contain from about 20 to 300 carbon atoms and preferably from 30 to 150 carbon atoms. An especially preferred polyolefin is polyisobutylene.

The lubricating oils of this invention contain an oil of lubricating viscosity and a complex which provides from about 5 to 30 millimoles/kg and preferably from 18 to 24 millimoles/kg of the oil-insoluble zinc cyclic hydrocarbyl dithiophosphates and from 1 to 15 weight percent and preferably from 3 to 8 weight percent of the alkenyl or alkyl succinimide.

The complex, the exact structure of which is not known, may be formed by reacting the zinc cyclic hydrocarbyl dithiophosphate and the succinimide together in a diluent in which both reactants are soluble. For example, the reactants may be combined in the proper ratio in a solvent such as toluene or chloroform, the solvent stripped off, and the complex thus formed may be added to the oil or the oil may be added prior to solvent stripping, i.e., the oil is added to the solvent-complex solution and the solvent subsequently stripped.

The diluent is preferably inert to the reactants and products formed and is used in an amount sufficient to insure solubility of the reactants and to enable the mixture to be efficiently stirred.

Temperatures for preparing the complex may be in the range of from 25° C. to 200° C. and preferably 25° C. to 80° C. Since the zinc cyclic hydrocarbyl dithiophosphates are essentially insoluble in oil, the complex may not be made in-situ in the oil, e.g., addition of the insoluble zinc cyclic hydrocarbyl dithiophosphate to an oil containing the appropriate ratio of a succinimide does not solubilize the dithiophosphate.

Alternately, the soluble cyclic hydrocarbyl zinc dithiophosphate-succinimide complexes of this invention are prepared by reacting the cyclic hydrocarbyl dithiophosphoric acid with the basic zinc compound and the oil-soluble alkenyl or alkyl mono- or bis-succinimide in an organic solvent.

In carrying out this process, the cyclic hydrocarbyl dithiophosphoric acid is added to a slurry containing a basic zinc compound and the succinimide in an organic hydrocarbon solvent. The components are reacted at a temperature of about 25° C. to 180° C. A promotor such as water or acetic acid may also be used to assist the reaction.

Preferably, the temperature is adjusted in order to azeotrope off any water formed during the course of the reaction, i.e., 80° C. to 140° C.

Typical examples of solvents which may be used include benzene, toluene, xylene, and the like.

Sufficient basic zinc compound is present to essentially neutralize the cyclic hydrocarbyl dithiophosphoric acid and is present in the reaction mixture in an amount of from about 0.7 to 1.3 equivalents per equivalent of the cyclic hydrocarbyl dithiophosphoric acid. Preferably, the basic zinc compound and the cyclic hydrocarbyl dithiophosphoric acid are present in an equivalent amount.

Weight percent ratios of alkenyl or alkyl mono- or bis-succinimides to zinc cyclic hydrocarbyl dithiophosphate in the complex in the range of 3:1 to 25:1 and preferably from 3:1 to 10:1 should be maintained. Lesser amounts of the succinimide will result in haziness and precipitation of the zinc cyclic hydrocarbyl dithiophosphates.

Additive concentrates are also included within the scope of this invention. They usually include from about 90 to 10 weight percent of an oil of lubricating viscosity and are normally formulated to have about 10 times the additive concentration that would be used in the finished lubricating oil composition. Usually, this will be a sufficient amount of complex to supply about 50 to 300 millimoles/kg of the zinc cyclic hydrocarbyl dithiophosphate and 10 to 150 weight percent of the alkenyl or alkyl succinimide. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although any oil of lubricating viscosity can be used.

Suitable lubricating oils which can be used to prepare a lubricating oil composition or concentrate are oils of lubricating viscosity derived from petroleum or synthetic sources. The oils can be paraffinic, naphthenic, halo-substituted hydrocarbons, synthetic esters, or combinations thereof. Oils of lubricating viscosity have viscosities in the range from 35 to 50,000 SUS at 100° F., and more usually from about 50 to 10,000 SUS at 100° F.

Other conventional additives which can be used in combinations with the additive combination of this invention include oxidation inhibitors, antifoam agents, viscosity index improvers, pour-point depressants, and the like. These include such compositions as chlorinated wax, benzyl disulfide, sulfurized sperm oils, sulfurized terpene, phosphorus esters such as trihydrocarbon phosphites, metal thiocarbamates such as zinc dioctyldithiocarbamate, polyisobutylene having an average molecular weight of 100,000, etc.

The lubricating oil compositions of the invention are useful for lubricating internal combustion engines, automatic transmissions and as industrial oils such as hydraulic oils, heat-transfer oils, torque fluids, etc. The lubricating oils can not only lubricate the engines but, because of their dispersancy properties, help maintain a high degree of cleanliness of the lubricated parts.

The following examples are provided to illustrate the invention. It is to be understood that they are provided for the sake of illustration and not as a limitation on the scope of the invention.

EXAMPLES

Example 1

To a 2-liter, 3-necked flask equipped with a stirrer, nitrogen inlet, dropping funnel and condenser containing 600 ml of toluene and 222 gm (1.0 mole) of $P_2S_5$ was added 208.3 gm (2.0 mole) of 2,4-pentanediol over a period of 25 minutes. The temperature rose to 43° C. with a large volume of $H_2S$ evolving. After stirring the reaction mixture under nitrogen for 0.5 hour, the reaction mixture was heated to reflux for about 2 hours. The reaction mixture was then filtered and the filtrate stripped of solvent in a Rotary Evaporator under full pump vacuum and a water-bath temperature up to 80° C. The product, a greenish-yellow oily liquid, weighed 384.5 gm. Acid number of product was 249; 239 mg KOH/gm and $^{31}$PNMR confirmed the cyclic nature of the product having the formula:

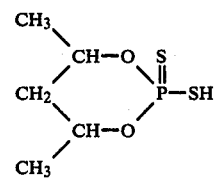

In a similar manner, cyclic hydrocarbyl dithiophosphoric acids from neopentyl glycol and 2-ethyl-1,3-hexanediol were prepared by substituting an equivalent amount of the respective glycol for the 2,4-pentanediol in the above reaction.

Example 2

To a 2-liter, 3-necked flask equipped with a stirrer, nitrogen inlet, dropping funnel and Dean-Stark trap containing 480 ml toluene, 495 gm of polyisobutenyl succinimide (prepared by reacting polyisobutenyl succinic anhydride and triethylene-tetramine wherein the number average molecular weight of the polyisobutenyl was about 940 and in a mole ratio of amine to anhydride of 0.90) and 20.34 gm (0.25 mole) of zinc oxide at a temperature of 50° C. was added 115 gm (0.5 mole) of the cyclic hydrocarbyl dithiophosphoric acid of 2,4-pentanediol of Example 1 over a period of 45 minutes. The temperature was elevated to about 75° C. and maintained for 3.5 hours after which the temperature was raised to reflux for 1.5 hours. The reaction mixture was cooled, diluted with 200 ml toluene, heated to 50° C. and filtered. The clear filtrate was stripped in a Rotary Evaporator under a full pump vacuum and a water-bath temperature up to 82° C. to yield zinc cyclic hydrocarbyl dithiophosphate of 2,4-pentanediol-succinimide complex.

In a similar manner, the zinc cyclic hydrocarbyl dithiophosphate neopentyl glycol-succinimide complex and the zinc cyclic hydrocarbyl dithiophosphate of 2-ethyl-1,3-hexanediol-succinimide complex were prepared by substituting an equivalent amount of the cyclic hydrocarbyl dithiophosphoric acid of neopentyl glycol and 2-ethyl-1,3-hexanediol, respectively, for the cyclic hydrocarbyl dithiophosphoric acid of 2,4-pentanediol in the above procedure.

Example 3

A. Dithiophosphoric Acid Of 2-Ethyl-1,3-Hexanediol

A 5-liter, 3-necked flask equipped with a stirrer, nitrogen inlet, dropping funnel and condenser containing 900 ml xylene and 86 gm (0.387 mole) of $P_2S_5$ was heated with stirring to 85° C. under a nitrogen atmosphere. To the reaction mixture was added 112.5 gm (0.769 mole) 2-ethyl-1,3-hexanediol dissolved in 1350 ml xylene over about a 7-hour period. The reaction mixture was heated an additional 5 hours at 85° C. and was allowed to cool for about 12 hours. The reaction mixture was then filtered and the filtrate stripped of solvent in a Rotary Evaporator under full pump vacuum and a water bath up to 85° C. The product, a yellow liquid, weighed 189.6 gm.

B. Zinc Salt of Dithiophosphoric Acid of 2-Ethyl-1,3-Hexanediol

To a 1-liter, 3-necked flask equipped with a stirrer, nitrogen inlet, dropping funnel and condenser was added 60.9 gm (0.178 equivalent weight) of dithiophosphoric acid of 2-ethyl-1,3-hexanediol prepared in Step A, 31.18 gm (0.38 equivalent weight) ZnO, 2 ml water, and 150 ml of xylene. To the reaction mixture which was heated to about 70° C. was added 121 gm (0.357 equivalent weight) of dithiophosphoric acid of 2-ethyl-1,3-hexanediol in 100 ml xylene over a period of 65 minutes. Heating was continued for another 2 hours after which the temperature was lowered to 40° C. and 2 ml of water and 3.1 gm ZnO was added to the reaction mixture. The temperature was elevated to about 70° C. and maintained for about 5 hours. The reaction mixture was cooled and filtered. The filtrate was stripped in a Rotary Evaporator under full pump vacuum and a water bath up to 85° C. The product, a viscous yellow liquid weighed 197.51 gm; % Zn found, 11.21%; % P found, 11.36%.

Example 4

To 80 ml toluene at about 25° C. were added 2.13 gm of the zinc salt of dithiophosphoric acid of 2-ethyl-1,3-hexanediol of Example 3-B and 6.95 gm of polyisobutenyl succinimide (prepared by reacting polyisobutenyl succinic anhydride and triethylene-tetramine wherein the number average molecular weight of the polyisobutenyl was about 940, in a mole ratio of amine to anhydride of 0.90). To this clear solution was added 20 gm of oil (RPM 130N/480N) and the toluene was stripped off under vacuum.

A formulated oil blend was prepared from this oil concentrate containing the oil-soluble complex of this invention (sufficient to supply 18 mmoles/kg of the zinc salt of dithiophosphoric acid of 2-ethyl-1,3-hexanediol and 3.5% of the polyisobutenyl succinimide) by adding to the concentrate 1.54 gm (30 mmoles/kg) magnesium sulfonate, 1.72 gm (20 mmoles/kg) of a calcium phenate and 13 gm (6.5%) of polymethacrylate V.I. improver and sufficient oil to bring the total composition up to 200 gm. The oil blend thus prepared was bright and clear. The zinc salt of dithiophosphoric and 2-ethyl-1,3-hexanediol above was not appreciably soluble in the oil.

Example 5

Various oil blends were prepared as indicated in Table 1 using Mid Continental Parrafic base oil (CC100N) and containing several of the zinc cyclic hydrocarbyl dithiophosphates alone and the corresponding zinc cyclic hydrocarbyl dithiophosphate-polyisobutenyl succinimide complexes of Examples 2 and 3.

TABLE 1

| Component | Amount (based on % Zn) | Observation |
|---|---|---|
| zinc cyclic hydrocarbyl dithiophosphate of 2,4-pentanediol | 3 mmoles/kg | solids present in oil |
| zinc cyclic hydrocarbyl dithiophosphate of neopentyl glycol | 3 mmoles/kg | solids present in oil |
| zinc cyclic hydrocarbyl dithiophosphate of 2-ethyl-1,3-hexanediol | 3 mmoles/kg | solids present in oil |
| zinc cyclic hydrocarbyl dithophosphate of 2,4-pentanediol-polyisobutenyl succinimide of triethylene-tetramine (3.5%) complex | 18 mmoles/kg | bright and clear oil solution |
| zinc cyclic hydrocarbyl dithiophosphate of neopentyl glycol-polyisobutenyl succinimide of triethylene-tetramine (3.5%) complex | 18 mmoles/kg | bright and clear oil solution |
| zinc cyclic hydrocarbyl dithiophosphate of 2-ethyl-1,3-hexanediol-polyisobutylene succinimide of triethylene-tetramine (3.5%) complex* | 18 mmoles/kg | bright and clear oil solution |

*The zinc salt of dithiophosphoric acid of 2-ethyl-1,3-hexanediol and the succinimide were first dissolved in toluene and after formation of the complex, the oil was added with subsequent removal of the toluene.

Example 6

Formulated oils containing the additives shown in Table 2 were prepared and tested in a Sequence III-D Test method (according to ASTM Special Technical Publication 315H). The compositions were prepared by adding each of the succinimide complexes of zinc cyclic hydrocarbyl dithiophosphates of 2,4-pentanediol and neopentyl glycol of Example 2 and 2-ethyl-1,3-hexanediol of Example 4 to a formulated oil in a sufficient amount to supply 18 mmoles/kg Zn and 3.5% of the succinimide.

The purpose of the test is to determine the effect of the additives on the oxidation rate of the oil and the cam and lifter wear in the valve train of an internal combustion engine at relatively high temperatures (about 149° C. bulk oil temperature during testing).

In this test, an Oldsmobile 350 CID engine was run under the following conditions:

Runs at 3,000 RPM/max run time for 64 hours and 100 lb load;
Air/fuel* ratio=16.5/1, using * GMR Reference fuel (leaded);
Timing=31° BTDC;
Oil temperature=300° F.;
Coolant temperature in=235° F.—out 245° F.;
30" of water of back pressure on exhaust;
Flow rate of jacket coolant=60 gal/min;
Flow rate of rocker cover coolant=3 gal/min;
Humidity must be kept at 80 grains of $H_2O$;
Air temperature controlled equal inlet equal 80° F.;
Blowby Breather Heat exchanger at 100° F.

The effectiveness of the additive is measured after 64 hours in terms of camshaft and lifter wear and percent viscosity increase.

The comparisons were made in a formulated base oil RPM 130N/480N at 85%/15% containing 30 mmoles/kg of a magnesium sulfonate, 20 mmoles/kg of a calcium phenate and 5.5% of a polymethacrylate V.I. improver.

TABLE 2

| | | Sequence III-D Test | | | |
| | | Cam + Lifter Wear × $10^{-3}$ In. | | Viscosity Increase % at 40 hr. | Viscosity Increase % at 64 hr. |
| Entry | Formulation | SF Spec. Max. (8) | SF Spec. Avg. (4) | | |
| --- | --- | --- | --- | --- | --- |
| 1 | 18 mmoles/kg zinc cyclic hydrocarbyl dithiophosphate of neopentyl glycol + 3.5% succinimide complex of Example 2 | 2.3 | 1.4 | 135 | 1553 |
| 2 | 18 mmoles/kg zinc cyclic hydrocarbyl dithiophosphate of 2,4-pentanediol + 3.5% succinimide complex of Example 2 | 1.8 | 2.2 | 265 | 4236 |
| 3 | 18 mmoles/kg zinc cyclic hydrocarbyl dithiophosphate of 2-ethyl-1,3-hexanediol + 3.5% succinimide complex of Example 4 | 1.9 | 1.1 | 103 | 307 |

Example 7

A formulated oil containing the succinimide complex of zinc cyclic hydrocarbyl dithiophosphate of 2,4-pentanediol of Example 2 was tested in a Sequence V-D Test method Phase 9-L (according to candidate test for ASTM). This procedure utilizes a Ford 2.3 liter four-cylinder engine. The test method simulates a type of severe field test service characterized by a combination of low speed, low temperature "stop and go" city driving and moderate turnpike operation. The effectiveness of the additives in the oil is measured in terms of the protection provided against sludge and varnish deposits and valve train wear. The results are indicated in Table 3.

The comparisons were made in a formulated base oil Cit-Con 100N/Cit-Con 200N at 55%/45% containing 30 mmoles/kg of a magnesium sulfonate, 20 mmoles/kg of a calcium phenate and 8.5% of a polymethacrylate V.I. improver. The succinimide complex was present in sufficient amount to supply 8.1 mmoles/kg Zn and 3.5% of the succinimide.

TABLE 3

| | Sequence V-D Test | | | |
| | Cam Lobe Wear × $10^{-3}$ | | Varnish | Sludge |
| Formulation | SF Spec. Max. (2.5) | SF Spec. Avg. (1.0) | SF Spec. Avg. (6.6) | SF Spec. Avg. (9.4) |
| --- | --- | --- | --- | --- |
| 8.1 mmoles/kg zinc cyclic hydrocarbyl dithiophosphate of 2,4-pentanediol + 3.5% succinimide complex of Example 2 | 1.1 | 0.8 | 6.86 | 9.7 |

What is claimed is:

1. A lubricating oil composition comprising a major amount of an oil of lubricating viscosity and a minor proportion sufficient to inhibit oxidation and corrosion of a complex prepared by reacting:
   (a) a zinc salt of a cyclic hydrocarbyl dithiophosphoric acid of the formula:

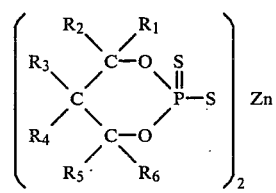

wherein $R_1$, $R_2$, $R_3$, $R_4$, $R_5$ and $R_6$ are the same or different and each is hydrogen or alkyl of 1 to 3 carbon atoms with the proviso that at least one of $R_1$ through $R_6$ is alkyl of from 1 to 3 carbon atoms; with (b) an oil-soluble alkenyl or alkyl mono- or bis-succinimide of the formula:

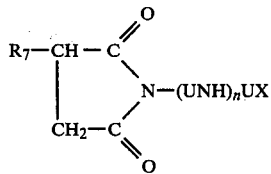

wherein X is amino or a group of the formula:

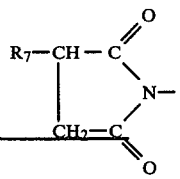

$R_7$ is an alkenyl or alkyl group containing from about 20 to 300 carbon atoms; U is alkylene containing 2 to 6 carbon atoms; and n is an integer of from 0 to 6;

wherein the weight ratio of (b) to (a) is in the range of from 3:1 to 25:1.

2. The composition of claim 1 wherein component (a) is present from about 5 mmoles to 30 mmoles and component (b) is present from about 1 percent to about 15 percent by weight.

3. The composition of claim 1 wherein component (a) is of the formula:

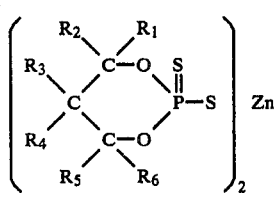

wherein R₁ and R₆ are hydrogen and each of R₂, R₃, R₄ and R₅ are hydrogen or alkyl of 1 to 3 carbon atoms with the proviso that at least one of R₁ through R₆ is alkyl of from 1 to 3 carbon atoms; and component (b) is of the formula:

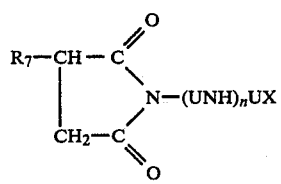

wherein X is amino or a group of the formula:

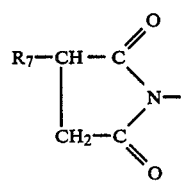

R₇ is polyisobutenyl; U is ethylene; and n is an integer of from 1 to 4.

4. The composition of claim 3 wherein component (a) is of the formula:

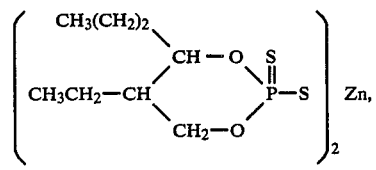

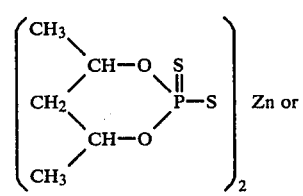

and component (b) is of the formula:

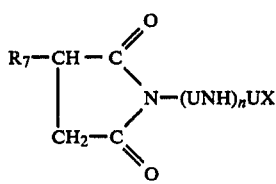

wherein X is amino or

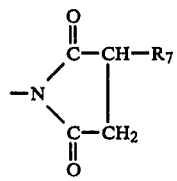

R₇ is polyisobutenyl; U is ethylene; and n is an integer of from 2 to 4.

5. The composition of claim 4 wherein in component (b) n is 2.

6. A lubricating oil concentrate comprising 10 percent to 90 percent by weight of an oil of lubricating viscosity and from about 10 percent to about 90 percent by weight of an oxidation and corrosion inhibiting complex prepared by reacting:

(a) a zinc salt of a cyclic dithiophosphoric acid of the formula:

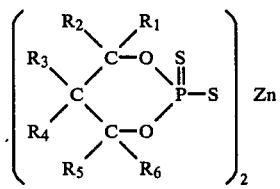

wherein R₁, R₂, R₃, R₄, R₅ and R₆ are the same or different and each is hydrogen or alkyl of 1 to 3 carbon atoms with the proviso that at least one of R₁ through R₆ is alkyl of from 1 to 3 carbon atoms; with (b) an oil-soluble alkenyl or alkyl mono- or bis-succinimide of the formula:

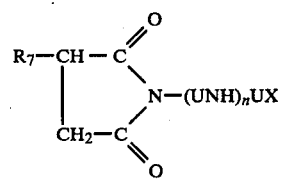

wherein X is amino or a group of the formula:

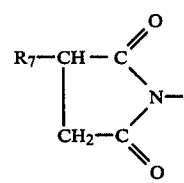

$R_7$ is an alkenyl or alkyl group containing from about 20 to 300 carbon atoms; U is alkylene containing 2 to 6 carbon atoms; and n is an integer of from 0 to 6;

wherein the weight ratio of (b) to (a) is in the range of from 3:1 to 25:1.

7. The lubricating oil concentrate of claim 6 wherein component (a) is of the formula:

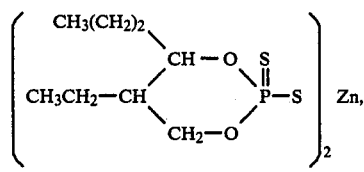

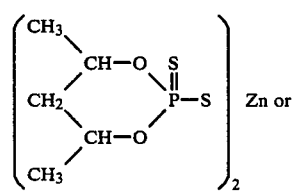

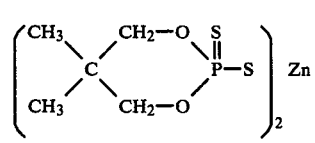

and component (b) is of the formula:

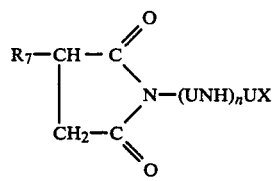

wherein X is amino or

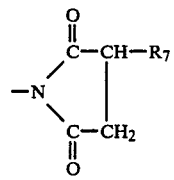

$R_7$ is polyisobutenyl; U is ethylene; and n is an integer of from 2 to 4.

8. The lubricating oil concentrate of claim 7 wherein in component (b) n is 2.

9. A composition comprising a complex prepared by reacting:

(a) a zinc salt of a cyclic dithiophosphoric acid of the formula:

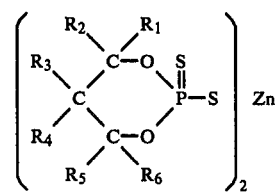

wherein $R_1$, $R_2$, $R_3$, $R_4$, $R_5$ and $R_6$ are the same or different and each is hydrogen or alkyl of 1 to 3 carbon atoms with the proviso that at least one of $R_1$ through $R_6$ is alkyl of from 1 to 3 carbon atoms; with (b) an oil-soluble alkenyl or alkyl mono- or bis-succinimide of the formula:

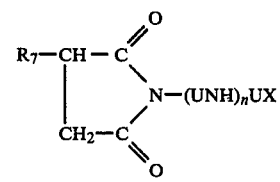

wherein X is amino or a group of the formula:

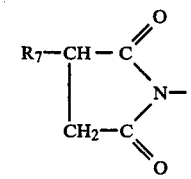

$R_7$ is an alkenyl or alkyl group containing from about 20 to 300 carbon atoms; U is alkylene containing 2 to 6 carbon atoms; and n is an integer of from 0 to 6;

wherein the weight ratio of (b) to (a) is in the range of from 3:1 to 25:1.

10. The composition of claim 9 wherein component (a) is of the formula:

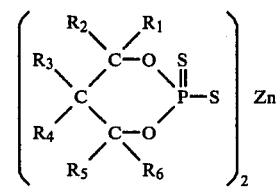

wherein $R_1$ and $R_6$ are hydrogen and each of $R_2$, $R_3$, $R_4$ and $R_5$ is hydrogen or alkyl of 1 to 3 carbon atoms with the proviso that at least one of $R_1$ through $R_6$ is alkyl of from 1 to 3 carbon atoms; and component (b) is of the formula:

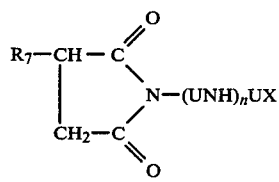
wherein X is amino or a group of the formula:
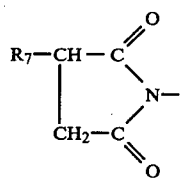
$R_7$ is polyisobutenyl; U is ethylene; and n is an integer of from 1 to 4.
11. The composition of claim 10 wherein component (a) is of the formula:
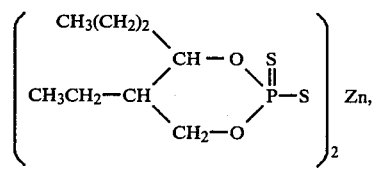
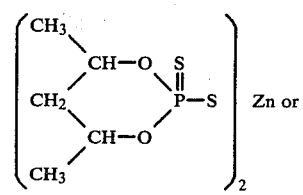
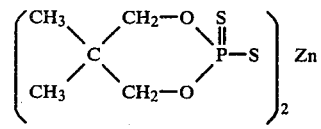
and component (b) is of the formula
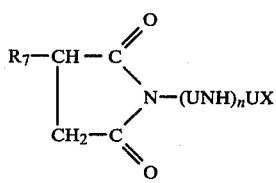
wherein X is amino or
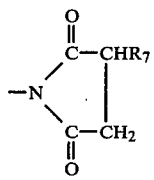
$R_7$ is polyisobutylene; U is ethylene; and n is an integer of from 2 to 4.
12. The composition of claim 11 wherein in component (b) n is 2.
* * * * *